United States Patent
Shiota

(10) Patent No.: US 6,798,861 B2
(45) Date of Patent: Sep. 28, 2004

(54) COMPUTER TOMOGRAPHY APPARATUS AND METHOD

(75) Inventor: Tadahiro Shiota, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 69 days.

(21) Appl. No.: 10/159,389

(22) Filed: May 30, 2002

(65) Prior Publication Data

US 2002/0191736 A1 Dec. 19, 2002

(30) Foreign Application Priority Data

Jun. 1, 2001 (JP) .................................... 2001-166463

(51) Int. Cl.$^7$ ................................................ G21K 1/12
(52) U.S. Cl. ................................ 378/17; 378/4; 378/24
(58) Field of Search ............................... 378/4, 17, 22, 378/24

(56) References Cited

U.S. PATENT DOCUMENTS 5,023,895 A * 6/1991 McCroskey et al. ........... 378/4
6,470,068 B2 * 10/2002 Cheng ........................... 378/20

* cited by examiner

Primary Examiner—Craig E. Church
(74) Attorney, Agent, or Firm—Rankin, Hill, Porter & Clark LLP

(57) ABSTRACT

As the operator sets a direction of moving a turn table, a view field FOV (z) of an X-ray detector in the rotation axis direction of the turn table, and the number of imaging times n and gives a continuous imaging command, the imaging operation of collecting X-ray fluoroscopic data while rotating the turn table and the operation of moving the turn table in the setup direction by FOV (z) are repeated and imaging is conducted n times. Then, the provided data is reconstructed to provide tomograms. It is possible to provide a continuous tomogram even if a high imaging magnification is set to provide high-resolution three-dimensional data and a necessary region for the three-dimensional data cannot be covered in the field of view of the X-ray detector.

6 Claims, 2 Drawing Sheets

COMPUTER TOMOGRAPHY APPARATUS AND METHOD

BACKGROUND OF THE INVENTION

1. Field of the Invention

The present invention relates to a computer tomography apparatus using X-rays (X-ray CT apparatus) and a computer tomography method. More particularly, the present invention relates to an X-ray cone beam CT apparatus.

2. Description of the Related Art

An X-ray CT apparatus generally applies X-rays to a target object to be imaged while rotating the target object around an axis orthogonal to an X-ray optical axis between an X-ray source and an X-ray detector, and collects fluoroscopic images from every direction of 360 degrees. Reconstruction processing is performed for collected data, whereby an X-ray tomogram is provided.

An ordinary X-ray CT apparatus stores fluoroscopic image data of each of lines (each of slices) spread one-dimensionally from the X-ray source as the collected data and calculates the X-ray tomograms of the slices from the data.

In contrast, in a technique called cone beam CT (simply, cone CT), an X-ray detector having a two-dimensional effective field of view is used. Such an X-ray cone beam CT apparatus applies a cone-like X-ray beam to a target object to be examined while rotating the target object around the axis orthogonal to the X-ray optical axis of the X-ray source to obtain two-dimensional fluoroscopic images. The two-dimensional fluoroscopic images are collected at a time, whereby X-ray tomograms of multiple slices can be provided.

In the cone CT, the data provided by one imaging is increased drastically as compared with the ordinary CT in the related art. Thus, a time required for collecting the three-dimensional data of the target object can be shortened drastically as compared with the ordinary CT in the related art. However, to provide a high-resolution tomogram in a small region regardless of the ordinary CT or the cone CT, SOD (Source to Object Distance) of a distance from the X-ray source to a rotation axis center of the target object and SID (Source to Image Distance) of a distance from the X-ray source to the X-ray detector need to be adjusted for raising an imaging magnification of the fluoroscopic image. However, as the image magnification is thus raised, the field of view of the cone beam is reduced and only a small region tomogram can be provided. Therefore, it is difficult to obtain three-dimensional data of a comparatively large target object in a high resolution.

SUMMARY OF THE INVENTION

It is an object of the invention to provide a computer tomography apparatus and method that can easily collect high-resolution three-dimensional data over a wide region.

In order to accomplish the object above, the following means are adopted. According to the present invention, there is provided a computer tomography apparatus comprising: an X-ray source for applying a cone-like X-ray beam to a target object to be examined; a two-dimensional X-ray detector being disposed on an X-ray optical axis of the X-ray source so as to be opposed to the X-ray source, for obtaining X-ray fluoroscopic data of the target object; a turn table being disposed between the X-ray source and the two-dimensional X-ray detector, for mounting the target object thereon and rotating the target object around an axis orthogonal to the X-ray optical axis; a data processing section for reconstructing a plurality of tomograms of the target object cut on a plane orthogonal to a rotation axis of the turn table; a number-of-imaging-times setting section for setting the number of imaging times; and a move mechanism for moving the turn table in a rotation axis direction of the turn table by an effective view field of the two-dimensional X-ray detector each time an imaging is executed until the number of imaging times reaches the setup number of imaging times. Further, the above-mentioned computer tomography apparatus may comprises a direction setting section for setting a direction when the turn table is moved in the rotation axis direction thereof, wherein the move mechanism moves the turn table in the setup direction set by the direction setting section.

In the above-mentioned computer tomography apparatus, it is preferable that the data processing section concatenates the plurality of tomograms reconstructed to obtain three-dimensional data of the target object.

In the invention, the number of imaging times and the direction for moving the turn table are preset. Thus, the imaging operation of collecting 360-degree X-ray fluoroscopic data while rotating the turn table and the operation of moving the turn table in the rotation axis direction by the field of view in the rotation axis direction are automatically repeated. Therefore, even if the imaging magnification is raised and the view field in the rotation axis direction of the turn table is narrowed, fluoroscopic data provided by imaging a plurality of times are concatenated, thereby expanding the substantial view field in the rotation axis direction.

That is, imaging is performed as many times as the setup number of times while the turn table is moved in the rotation axis direction by the setup field view in the rotation axis direction at a time. Thus, equivalent data to that provided by imaging in the view field being a plurality of times (as many as the setup number of times) the actual field of view in width in the rotation axis direction of the turn table can be provided by the whole imaging data. Therefore, if the substantial field view in the rotation axis direction is narrowed as imaging is conducted at a high imaging magnification to provide a high-resolution tomogram, three-dimensional data over a wide region can be provided by increasing the number of imaging times.

Further, in the invention, a plurality of tomograms every imaging time provided by reconstructing fluoroscopic data collected by imaging each time are concatenated into three-dimensional data of the target object. Therefore, the provided three-dimensional data becomes high-resolution data having a wide field of view, and, for example, high-resolution three-dimensional data of a target object to be examined which is long in one direction, such as a bar-like or columnar target object, can be provided easily.

DETAILED DESCRIPTION OF THE INVENTION

Referring now to the accompanying drawings, there is shown a preferred embodiment of the invention.

Figure 1:
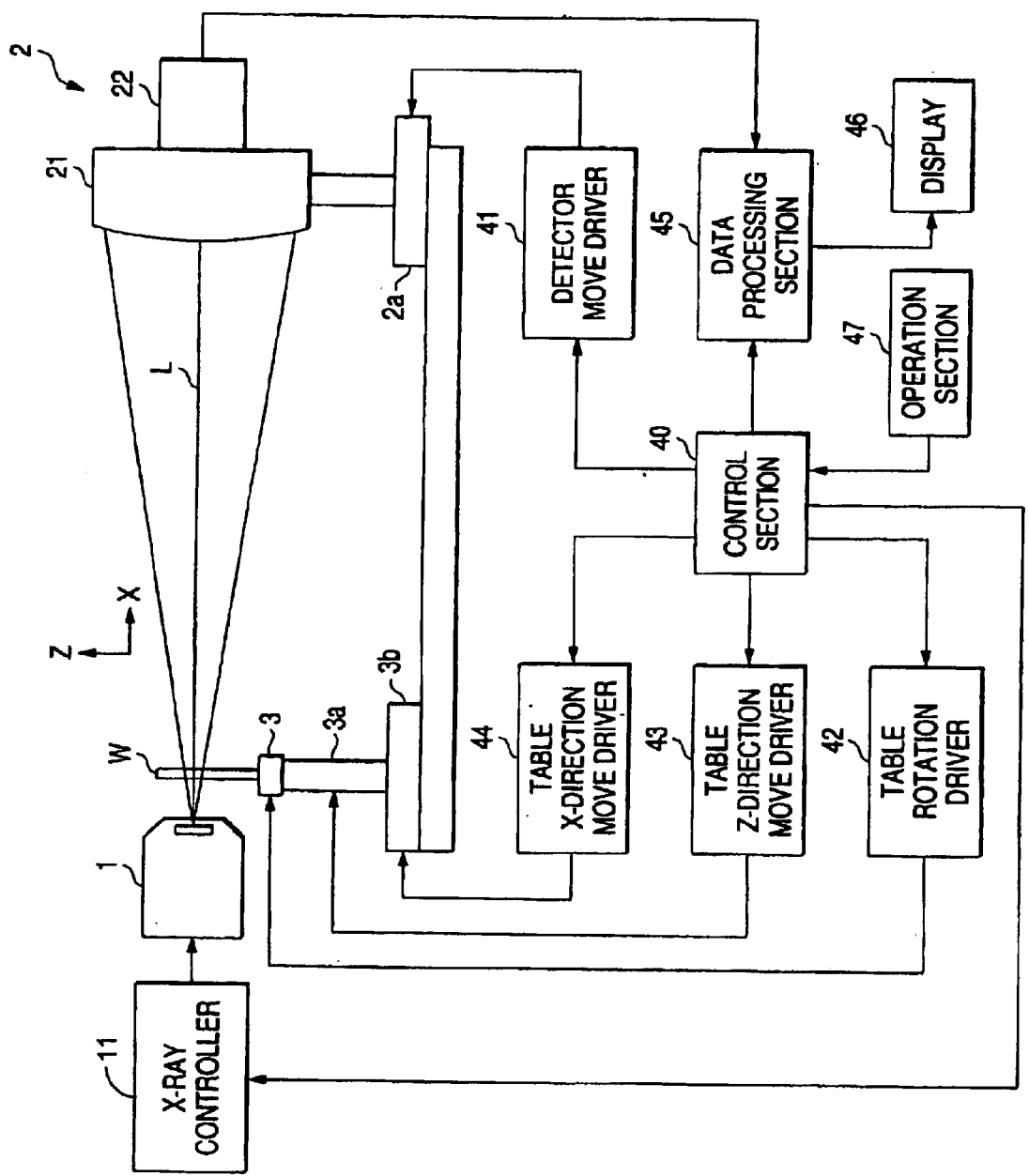
FIG. 1 is a diagram to show the configuration of a computer tomography apparatus according to an embodiment of the invention.

FIG. 1 is a diagram to show the configuration of a computer tomography apparatus according to an embodiment of the invention. FIG. 1 shows a mechanical configuration of the computer tomography apparatus with a schematic drawing and an electric configuration thereof with a block diagram.

The computer tomography apparatus has an X-ray source 1, a two-dimensional X-ray detector 2 and a turn table 3. The X-ray source 1 is placed in a state in which an X-ray optical axis L of the X-ray source is directed in a horizontal direction (x direction). The two-dimensional X-ray detector 2 is placed on the X-ray optical axis L so that it is opposed to the X-ray source 1. The turn table 3 is placed between the X-ray source 1 and the two-dimensional X-ray detector 2.

The X-ray source 1 is driven and controlled by a tube voltage and a tube current supplied from an X-ray controller 11, and outputs a cone-like X-ray beam along the horizontal optical axis L. The X-ray controller 11 contains a high-voltage generation circuit and is controlled by a control section 40.

The two-dimensional X-ray detector 2 includes an image intensifier 21 and a CCD camera 22. Each pixel data outputted from the CCD camera 22 is input to a data processing section 45. The two-dimensional X-ray detector 2 can be moved in the x direction by driving a detector move mechanism 2a comprising a motor (not shown). That is, the two-dimensional X-ray detector 2 can be moved toward or away from the X-ray source 1.

The turn table 3 mounts a target object W to be examined thereon and rotates the target object W. That is, the turn table 3 can be rotated around a rotation axis thereof, namely, along a vertical direction (z direction) by driving an internal motor (not shown). The turn table 3 can be moved in the z direction, namely, a rotation axis direction by driving a z direction move mechanism 3a comprising a motor (not shown). The turn table 3 also can be moved in the x direction by driving an x direction move mechanism 3b comprising a motor (not shown).

The motors of the detector move mechanism 2a, the turn table 3, and the z direction move mechanism 3a and the x direction move mechanism 3b of the turn table 3 are driven and controlled by drive signals supplied from a detector move driver 41, a table rotation driver 42, a table z direction move driver 43, and a table x direction move driver 44, respectively. Each of drivers 41, 42, 43, 44 is controlled by the control section 40.

Each pixel data outputted from the CCD camera 22 of the two-dimensional X-ray detector 2 is input to the data processing section 45. The data processing section 45 then performs various processing using the pixel data and performs reconstruction calculation of tomogram. The tomogram provided by the reconstruction calculation or the fluoroscopic image of the target object W is displayed on a display 46.

An operation section 47 of a keyboard, switches, and the like is connected to the control section 40. The operator can give various commands and enter various settings as described later by operating the operation section 47.

Figure 2:
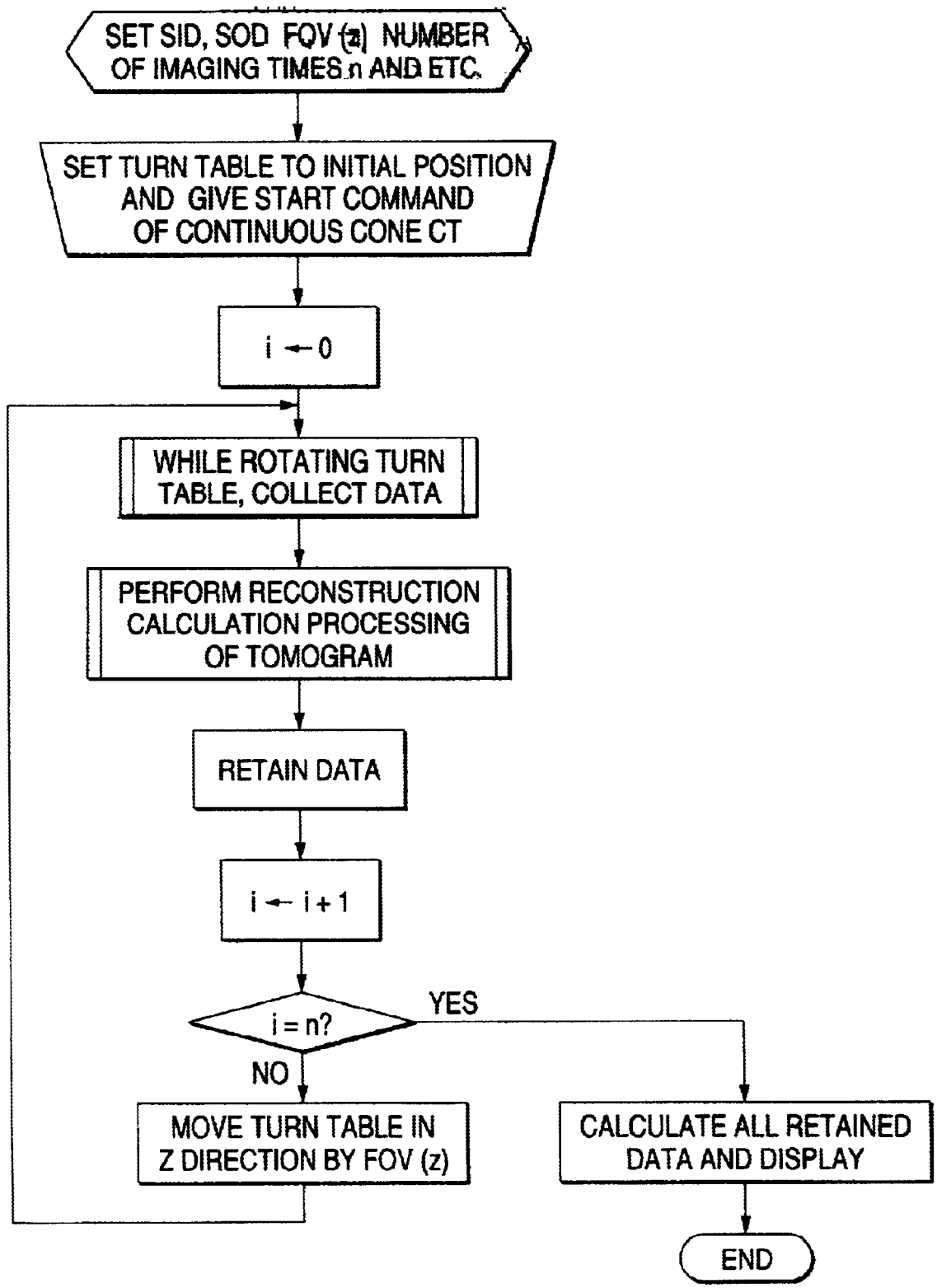
FIG. 2 is a flowchart to show a processing procedure according to the embodiment of the invention.

FIG. 2 is a flowchart to show a processing procedure according to the embodiment of the invention.

To begin with, while seeing the X-ray fluoroscopic image on the display 46, the operator operates the operation section 47 to move the two-dimensional X-ray detector 2 or the turn table 3 in the x direction through the detector move mechanism 2a or the x direction move mechanism 3b for adjusting the SID and the SOD to determine the imaging magnification and adjust X-ray conditions. At this time, if the imaging magnification is high and the field of view FOV (z) in the vertical direction cannot cover a region that provides the three-dimensional information of the target object W as one imaging procedure is conducted, the operator selects continuous cone CT item.

When the operator selects the continuous cone CT item, the operator sets an initial position (in the Z direction) of the turn table 3, a view field FOV (z) in the z direction, a direction when the turn table 3 is moved in the z direction from the initial position, the number of imaging times n, and other conditions to provide tomograms and then gives a start command of the continuous cone CT.

The CT apparatus calculates the maximum value of the view field FOV (z) in the z direction based on the x direction positions of the two-dimensional X-ray detector 2 and the turn table 3. The maximum view field FOV (z) in the z direction is displayed on the display 47. Thus, to set the view field FOV (z) in the z direction, the operator can use the maximum view field FOV (z) in the z direction which is displayed on the display 47 or set any desired view field FOV (z) with a narrower width in the z direction, considering distortion, etc., of the two-dimensional X-ray detector 2. In this case, the setup view field FOV (z) in the z direction is always set in a state in which a width from the view field center to one side thereof is equal to a width from the view field center to the other side thereof. Only the pixel data in the range of the setup view field FOV (z) are used to reconstruct the tomogram.

When the start command of the continuous CT is given, the turn table 3 is rotated with the turn table 3 set to the initial position and X-ray fluoroscopic data are collected. Upon completion of collecting the data, calculation of reconstruction processing of tomogram is performed and the provided data is retained. Next, when the number of imaging (data collection) times does not reach the setup number of imaging times n, the turn table 3 is moved by the setup view field FOV (z) in the z direction along the z direction in the setup direction, and then X-ray fluoroscopic data are collected. Calculation of reconstruction processing of tomogram is performed using the data, and the provided data is retained. When the number of imaging times reaches the setup number of imaging times n, all data retained so far are concatenated and the resultant data is displayed on the display 46 and the processing is terminated.

According to the embodiment of the invention described above, if the imaging magnification is raised to collect high space resolution data and thus the view field FOV (z) in the z direction is narrowed and cannot cover the region which can provide the three-dimensional data of the target object W as one imaging is conducted, the operator simply selects the continuous cone CT item and sets required conditions for performing the continuous cone CT. With such a simple operation, while the turn table 3 is automatically moved in the z direction, X-ray fluoroscopic data can be collected. Therefore, three-dimensional data in a wide region can be provided in a high resolution.

In the described embodiment, the invention is applied to the CT apparatus with the X-ray optical axis along the horizontal direction, but can also be applied to the CT apparatus with the X-ray optical axis along the vertical direction, of course. The point is that while the turn table is moved in the direction along the rotation axis of the turn table by the setup view field in the rotation axis direction at a time, X-ray fluoroscopic data can be collected.

As described above, according to the invention, the operator simply selects continuous cone CT item and sets the view field in the rotation axis direction of the turn table, the direction when the turn table is moved in the rotation axis direction, and the number of imaging times. Therefore, after one data collection is executed, automatically the turn table is moved in the setup direction by the view field in the rotation axis direction at a time and data collection is repeated. As a result, if the imaging magnification is raised to set a high resolution, a continuous tomogram over a wide region can be provided and three-dimensional information of a comparatively large target object can be provided in a high space resolution. Further, as the number of consecutive imaging times is increased, the limit on the field of view in the rotation axis direction of the turn table can be substantially eliminated.

What is claimed is:

1. A computer tomography apparatus comprising:
   an X-ray source for applying a cone-like X-ray beam to a target object to be examined;
   a two-dimensional X-ray detector being disposed on an X-ray optical axis of the X-ray source so as to be opposed to the X-ray source, for obtaining X-ray fluoroscopic data of the target object;
   a turn table disposed between the X-ray source and the two-dimensional X-ray detector, said turn table having the target object mounted thereon and being operable to rotate the target object around an axis orthogonal to the X-ray optical axis;
   a data processing section for reconstructing a plurality of tomograms of the target object cut on a plane orthogonal to a rotation axis of the turn table;
   a number-of-imaging-times setting section for setting a number of imaging times; and
   a move mechanism for moving the turn table in a rotation axis direction of the turn table by an effective view field of the two-dimensional X-ray detector each time an imaging is executed until the number of imaging times reaches the set number of imaging times.

2. The computer tomography apparatus as claimed in claim 1, further comprising:
   a direction setting section for setting a direction when the turn table is moved in the rotation axis direction,
   wherein the move mechanism moves the turn table in the direction set by the direction setting section.

3. The computer tomography apparatus as claimed in claim 1, wherein the data processing section concatenates the plurality of tomograms reconstructed to obtain three-dimensional data of the target object.

4. A computer tomography method using a computer tomography apparatus including an X-ray source, a turn table, and a two-dimensional X-ray detector, the method comprising:
   setting a number of imaging times and an effective view field of the X-ray detector;
   applying a cone-like X-ray beam to a target object to be examined mounted on the turn table while rotating the target object around an axis orthogonal to an X-ray optical axis;
   collecting X-ray fluoroscopic data of the target object and reconstructing a tomogram of the target object cut on a plane orthogonal to a rotation axis of the turn table;
   moving the turn table in a rotation axis direction of the turn table by the effective view field of the two-dimensional X-ray detector if the number of imaging times does not reach the set number of imaging times and repeating the collecting step.

5. The computer tomography method as claimed in claim 4, further comprising:
   setting a direction when the turn table is moved in the rotation axis direction of the turntable.

6. The computer tomography method as claimed in claim 4, further comprising:
   concatenating a plurality of tomograms reconstructed to obtain three-dimensional data of the target object.

* * * * *